(12) United States Patent
Banavali et al.

(10) Patent No.: US 8,685,881 B2
(45) Date of Patent: Apr. 1, 2014

(54) CATALYST FOR TRANSESTERIFICATION PROCESS

(75) Inventors: Rajiv Banavali, Rydal, PA (US); Jose Trejo, Lansdale, PA (US)

(73) Assignee: Rohm and Haas Company, Philadelphia, PA (US)

(*) Notice: Subject to any disclaimer, the term of this patent is extended or adjusted under 35 U.S.C. 154(b) by 588 days.

(21) Appl. No.: 12/592,178

(22) Filed: Nov. 20, 2009

(65) Prior Publication Data

US 2010/0130769 A1    May 27, 2010

Related U.S. Application Data

(60) Provisional application No. 61/199,958, filed on Nov. 21, 2008.

(51) Int. Cl.
*B01J 23/02* (2006.01)
*C11C 3/00* (2006.01)
*B01J 35/02* (2006.01)
*C07C 67/02* (2006.01)

(52) U.S. Cl.
CPC .............. *B01J 23/02* (2013.01); *B01J 2523/33* (2013.01); *B01J 35/02* (2013.01); *C07C 67/02* (2013.01)
USPC ............................ 502/183; 502/174; 554/169

(58) Field of Classification Search
CPC ........ B01J 23/02; B01J 2523/23; Y02E 50/13
See application file for complete search history.

(56) References Cited

U.S. PATENT DOCUMENTS

| 6,818,026 B2 | 11/2004 | Tateno et al. |
| 2007/0282119 A1 | 12/2007 | Matson et al. |

FOREIGN PATENT DOCUMENTS

| EP | 1 785 478 A | 5/2007 |
| JP | 2001/271090 A | 10/2001 |
| WO | WO 03/087279 A2 | 10/2003 |
| WO | WO 2006/134845 | 12/2006 |
| WO | WO 2007/025360 A2 | 3/2007 |
| WO | WO 2007/140395 A2 | 12/2007 |
| WO | WO 2008/029132 A1 | 3/2008 |

OTHER PUBLICATIONS

Furnas, C.C., The rate of calcinatin of limestone, 1931, Industrial and Engineering Chemistry, vol. 23, No. 5, pp. 534-538.*
Kouzu, M., et al, "Calcium oxide as a solid base catalyst for transesterification . . . " Fuel (2007), doic 10.1016/j.fue1.2007.10.019.
Gryglewicz, S., "Alkaline-earth metal compounds as alcoholysis catalysts for ester oils synthesis" Applied Catalysis A: General 192 (2000) pp. 23-28.
Kouzu, M., et al. "Active phase of calcium oxide used as solid base catalyst for transesterification . . . " Applied Catalysis A: General 334 (2008) pp. 357-365.
Nobutake, N., et al. "Transesterfication of Soybean Oil Using Combusted Oyster Shell Waste as a Catalyst" Bioresource Technology 100 (2009) pp. 1510-1513.
Zhu, H., et al. "Preparation of Biodiesel Catalyzed by Solid Super Base of Calcium Oxide and Its Refining Process" Chinese Journal of Catalysis, 2006. vol. 27(5) pp. 391-396.
Duo, W., et al. "Crystallization and Fracture: Formation of Product Layers in Sulfation of Calcined Limestone" Powder Technology 111(2000) pp. 154-167.
Wei, Z., et al. "Application of Waste Eggshell as Low-Cost Solid Catalyst for Biodiesel Production" Bioresource Technology 100 (2009) pp. 2883-2885.
Suppes, G.J., et al. "Calcium Carbonate Catalyzed Alcoholysis of Fats and Oils" JAOCS, vol. 78, No. 2 (2001) pp. 139-145.

* cited by examiner

*Primary Examiner* — Yate K Cutliff
(74) *Attorney, Agent, or Firm* — Carl P. Hemenway

(57) ABSTRACT

The present invention relates to a method for producing esters from triglycerides by using solid heterogeneous catalysts comprised of calcined calcium carbonate, particularly for obtaining biodiesel.

4 Claims, No Drawings

CATALYST FOR TRANSESTERIFICATION PROCESS

This application claims the benefit of priority under 35 U.S.C. §119(e) of U.S. Provisional Patent Application No. 61/199,958 filed on Nov. 21, 2008.

The present invention relates to a method for producing esters from triglycerides by using solid heterogeneous catalysts, particularly for obtaining biodiesel.

Biodiesel, used as fuel in diesel engines, is constituted by a mixture of esters of fatty acids obtained by a reaction of transesterification of triglycerides with an aliphatic alcohol and subsequent separation from a glycerin byproduct.

The transesterification reaction for producing biodiesel is generally performed by using bases of alkaline metals, such as for example NaOH, KOH, NaOCH$_3$, and KOCH$_3$ as catalysts.

Currently, the cost of biodiesel is greater than the cost of petroleum-derived diesel fuel and therefore an improvement of the process which leads to lower costs of biodiesel fuel is of interest.

One way in which to improve the biodiesel process is to use comparatively less expensive materials for the reaction while maintaining a constant or improved level of performance. One such attempt to use less expensive catalysts is disclosed in W0 2006/134845 which discloses the use of solid base catalysts for the production of biodiesel fuel. The reference further discloses the use of the relatively inexpensive CaO material as a transesterification catalyst. The problem with this catalyst is that in continuous runs on the biodiesel production in the transesterification reaction step, the material expands and causes problems with the flow of reactants, and creates pressure drops. Moreover, the expansion of the catalyst materials over time produces fine suspensions which make it difficult to separate the ester and glycerin phases and can eventually cause blockages and damage the reaction equipment if a packed bed reactor is used. Additionally, the synthesis of the catalyst in WO2006/134845 is sensitive to air and must be manufactured under nitrogen or helium atmosphere.

The present invention solves the problems of the art by providing a method for inexpensively producing esters from triglycerides by employing a solid heterogeneous catalyst derived from partially calcined limestone materials that does not need to be manufactured under inert gases and may be run continuously without potentially harming the production equipment over time.

Thus, in a first aspect of the present invention there is provided a solid heterogeneous transesterification catalyst composition comprising:

a calcined calcium carbonate mixture wherein the calcined calcium carbonate mixture comprises i) calcium carbonate wherein the calcium carbonate has a mean crystal size in the range of 350-500 Å and is present in the mixture in an amount in the range of 70-95% based on total weight of the mixture;

ii) calcium oxide wherein the calcium oxide has an mean crystal size in the range of 50-300 Å and is present in the mixture in an amount in the range of 5-30% based on total weight of the mixture; and iii) calcium hydroxide wherein the calcium hydroxide has a mean crystal size in the range of 110-300 Å and is present in the mixture in an amount in the range of 5-25% based on total weight of the mixture.

In a second aspect of the present invention there is provided a method for making a solid heterogeneous transesterification catalyst composition comprising:

i) providing a limestone material that comprises at least 95% calcium carbonate ii) calcining the limestone material at a temperature of at least 600° C., under air, for a period no greater than 2 hours wherein the calcinations is not performed under inert gas.

4. In a third aspect there is provided A method for producing esters of fatty acids and glycerin, comprising:

i) providing a solid heterogeneous transesterification catalyst composition comprising a calcined calcium carbonate mixture wherein the calcined calcium carbonate mixture comprises a) calcium carbonate wherein the calcium carbonate has a mean crystal size in the range of 350-500 Å and is present in the mixture in an amount in the range of 70-95% based on total weight of the mixture;

b) calcium oxide wherein the calcium oxide has an mean crystal size in the range of 50-300 Å and is present in the mixture in an amount in the range of 5-30% based on total weight of the mixture; and c) calcium hydroxide wherein the calcium hydroxide has a mean crystal size in the range of 110-300 Å and is present in the mixture in an amount in the range of 5-25% based on total weight of the mixture;

ii) providing a reaction mixture comprising a triglyceride and an aliphatic alcohol; and iii) contacting the reaction mixture with the solid heterogeneous transesterification catalyst composition wherein the reaction mixture reacts to form a product further wherein the product comprises aliphatic alcohol, biodiesel and glycerol.

All percentages are weight percentages, and all temperatures are in ° C., unless otherwise indicated. Weight percentages of the calcined limestone catalyst of the present invention are based on dry resin.

An "alkyl" group is a saturated hydrocarbyl group having from one to twenty carbon atoms in a linear, branched or cyclic arrangement. Substitution on alkyl groups of one or more halo, hydroxy, alkoxy or nitro groups is permitted; alkoxy substituents may in turn be substituted by one or more halo substituents where possible. Preferably, alkyl groups have no halo substituents, and in one preferred embodiment, alkyl groups are unsubstituted and acyclic.

"Triglycerides" used in this invention are fats or oils comprising glycerine triesters of fatty acids. Preferably, triglycerides are in the form of vegetable oils, but animal fats can also be used as a starting material. Triglycerides also may contain free fatty acids. Fatty acids are acyclic aliphatic carboxylic acids containing from 8 to 20 carbon atoms; typically, they contain from 12 to 18 carbon atoms; with carbon-carbon bonds, the fatty acids may be saturated, monounsaturated or polyunsaturated (typically 2 or 3 carbon-carbon double bonds). Natural fats may also contain small amounts of other esterified, or free fatty acids, as well as small amounts (1-4%) of phospholipids, e.g., lecithin, and very small amounts (<1%) of other compounds, e.g., tocopherols.

The solid heterogeneous catalyst of the present invention comprises calcined calcium carbonate (CaCO$_3$), also referred to herein as calcined limestone. The limestone material of the present invention prior to calcinations comprises at least 95% by weight CaCO$_3$. The calcined limestone is calcined at a temperature of at least 600° C. Alternatively the limestone is calcined at a temperature greater than 700° C. or alternatively at greater than 800° C.

The solid heterogeneous catalyst of the present invention is calcined under air with no need to add inert gases such as nitrogen or helium as described in the prior art. The catalyst may be held at constant temperature during calcinations.

Such hold times may be equal to or less than 2 hours and alternatively equal to or less than 1 hour. Advantageously, the reduced hold time for calcination needed to make his catalyst reduces the energy consumption and increases cost efficiency of the overall transesterification process.

Advantageously, the limestone catalyst used in the method of the present invention, once calcined, comprises a combination of three elements: calcium oxide (CaO), calcium hydroxide ($Ca(OH)_2$), and calcium carbonate ($CaCO_3$).

The %-w of each element can be measured by XRD (X ray diffraction method). The catalyst of the present invention comprises: $CaCO_3$ ranging in an amount from 70-95%, or alternatively 70-85%, or alternatively 75-80%. Furthermore, the catalyst comprises CaO in an amount of less than 25%, alternatively less than 20%, alternatively less than 15% but in no case less than 5%. $Ca(OH)_2$ is present in an amount less than 5%. These ranges aid to avoid excessive volume change during the continuous biodiesel production in a packed bed reactor.

The catalyst used in the present invention are characterized by a surface area ranging from 0.1 to 10.0 $m^2/g$, or alternatively from 0.5 to 5.0 $m^2/g$; a pore volume between 0.001 and 0.005 $m^2/g$, or alternatively from 0.002 to 0.003 $m^2/g$; with a pore size between 70 to 500 Å or alternatively from 200 to 300 Å; and with a particle size greater than 100 um, alternatively greater than 400 um or greater than 800 um. Furthermore, the elements of the catalyst have a mean crystal size in the ranges of: $CaCO_3$ (350-500 Å), CaO (50-300 Å), $Ca(OH)_2$ (110-300 Å) respectively. As used herein by "mean crystal size" is meant the crystal size estimated by the Scherrer Equation based upon the data obtained by X rays diffraction (XRD) method.

The method according to the present invention comprises in particular the steps of mixing the triglyceride(s) with an aliphatic alcohol, placing the mixture in contact with the solid catalyst of the present invention, and then heating to the reaction temperature.

Specifically, the method of the present invention comprises mixing the triglyceride(s) with an aliphatic alcohol in a ratio of g-(Triglyceride)/g-(Alcohol) of approximately 60/40, or alternatively 75/25 or alternatively 90/10.

The reaction mixture of the present invention may be fed into any reactor systems known to those of ordinary skill in the art. Examples of suitable reactor systems include but are not limited to single agitated reactor, continuous stirred reactors (CSTR) in series, or a plug flow reactor.

In the case of a packed bed reactor, the alcohol and the triglyceride are mixed and then fed into the column. The LHSV ($h^{-1}$ (Linear Hourly Space Velocity=Volume of Catalyst/Flow Rate of the liquid) range from greater than 0.01 to 2, or alternatively greater than 0.50, or alternatively greater than 2.

In one embodiment of the invention, the reaction column is heated to a temperature ranging from 50° C. to 150° C. When the temperature is at least 50° C. alternatively at least 65° C. alternatively grater than 90° C., the reaction mixture is fed through the packed bed column. Any method known to those of ordinary skill in the art may be used to feed the mixture through the packed bed column.

In one embodiment of the invention, the effluent from the column can be filtered, decanted and two distinct layers obtained. Layer 1 generally consists, in large part, the alcohol. Layer 2 generally consists, in large part, the biodiesel fuel and glycerol byproduct. The effluent may then be distilled to remove the alcohol. The recovered alcohol may optionally be reused in the process. After the alcohol is removed, another two distinct layers are obtained. The top layer comprises primarily the biodiesel fuel and the bottom layer comprises primarily glycerol byproduct. The glycerol obtained from the transesterification reaction may be removed as part of a separate liquid phase, or by any other suitable separation technique, e.g., centrifugation, distillation and could be purified to USP grade by other methods.

The two layers are then separated. In one embodiment, the reaction mixture obtained is highly converted (>97%) to biodiesel which is isolated and may be further purified using methods known to the skilled in the art. One or more ion exchange resins may optionally be used to remove residual glycerol and cations such as Na, K, Mg and Ca and to produce a biodiesel product with increased purity. The resultant biodiesel has a purity that meets minimum ASTM D6584 standard grade.

The method according to the present invention can also comprise an additional step of transesterification of the unreacted glycerides present in the ester phase.

In the method according to the present invention, the reaction can be performed in batch or in continuous fashion, and in reactors known to those of ordinary skill in the art. Suitable reactor types include but are not limited to agitated or fixed-bed reactors.

The following examples are suitable to illustrate the invention and must not be considered as limiting its scope.

Test Methods

Volume Expansion Measurement in Column During Continuous Run:

Volume Expansion Measurement: The column used in our experiments was a glass column. The internal diameter of the glass column used was 2.5 cm. The height of the bed was measured in time and the plot of %-Volume Expansion vs Bed volumes of liquid passed through the bed was reported.

Gas Chromatography (GC) Method

The GC method is used for calculating the relative conversion to biodiesel from triglycerides. The chromatographic conditions were the following: column:15 m×0.53 mm id, 0.25 u fil, RTX-1 (methyl silicone), temperature program: 50(1)-15° C./min-350 (10), Injection: 1:1 Split w/focus liner containing glass wool, Injection Temperature: 260° C., Detector Temperature: 300° C., Carrier Gas Flow: helium, 15 ml/min., 6 psi back pressure, 1:1 split, Purge flow: 24 ml/min, Injection Volume:1 microliter, Detector: FID, $H_2$ flow 30 ml/min, air 300 ml/min and Make-up flow: 15 ml/min.

Sample Preparation: The reaction mixture from the reactor or column was screened through a filtered of 45 um screen weighed and equal weight of THF to sample was added. 100 mg of sample was added to an empty vial, let evaporate at room temperature for 10 minutes, added 10 ml (80/20 heptane/THF) solution, 1 ml solution into autosampler vial where the vial was capped. 50 uL of derivatizing agent (MSTFA: N-Methyl-N-trifluoroacetamide) was injected into the vial. The mixture was agitated and reacted for 20 minutes prior to GC injection.

Conversion Calculation: The %-w obtained from the triglyceride, diglyceride and monoglyceride is ratio to the fatty acid methyl ester (FAME)%-w. The conversion is expressed as: %-conversion=(%-w MGL+%-w-DGL+%-w TGL)/(%-FAME)*100.

MGL=monoglyceride, DGL=diglyceride, TGL=triglyceride and FAME=fatty acid ester.

ASTM D6584—Quality Standards of Biodiesel

X-Ray Fluorescence ("XRF")

The limestone samples were analyzed using a Philips/PANalytical PW2404 Wavelength Dispersive X-Ray Fluorescence Spectrometer from PANalytical, Almelo, The Netherlands. The samples were dried overnight at 110° C. Approximately 1-1.5 g of each sample was weighed in a XRF sample cup with polypropylene film and analyzed under helium. The results were calculated using a Uniquant software package from Omega Data Systems by, Neptunus 2 NL-5505 NH Veldhoven, The Netherlands, which is a standardless quantitation package. Results were calculated assuming the elements were present in their oxide form except Ca, which is assumed to be $CaCO_3$. The sample is also assumed to be all inorganic. In XRF, an x-ray beam is focused on the sample, which displaces inner shell electrons; outer shell electrons replace the inner shell electrons and emit light during this process (or fluorescence) which is equal to the energy difference between them. The wavelength of light emitted is unique to each element and the intensity of the light emitted is proportional to the concentration of the element. Wavelength Dispersive XRF spectrometers use diffraction crystals to separate the various wavelengths of light emitted

EXAMPLES

Example 1

Limestone chips were calcined to prepare the transesterification catalyst by the following procedure. 150 g of dry limestone chips 0.4-0.7 mm were calcined at 800° C. for 6 hours under air, cooled down to 60° C. in 6 hours and packed. See Table 1.0

Example 2

Limestone chips were calcined to prepare the transesterification catalyst by the following procedure. 150 g of dry limestone chips 0.4-0.7 mm were calcined at 800° C. for 2 hours under air, cooled down to 60° C. in 6 hours and packed. See Table 1.0

Example 3

Limestone chips were calcined to prepare the transesterification catalyst by the following procedure. 150 g of dry limestone chips 0.4-0.7 mm were calcined at 800° C. for 1 hour under air, cooled down to 60° C. in 6 hours and packed. See Table 1.0

TABLE 1.0

| Example | Calculated %-w of each crystal phase on the catalyst. | | | Calculated Crystal Size by XRD | | | Calcination Weight Loss |
|---|---|---|---|---|---|---|---|
| | $CaCO_3$ (%-w) | CaO (%-w) | $Ca(OH)_2$ (%-w) | $CaCO_3$ (Å) | CaO (Å) | $Ca(OH)_2$ (Å) | Weight Loss after calcination |
| 1 | 0 | 74 | 25 | ND | 815 | 105 | 40 |
| 2 | 46 | 35 | 19 | 490 | 190 | 250 | 24 |
| 3 | 72 | 23 | 4 | 450 | 200 | 160 | 10 |
| Limestone | 97 | 0 | 1 | NR | NR | NR | NR |

Table 1.0 depicts the amounts of CaO, $CaCO_3$ and $Ca(OH)_2$ present as calculated by X-Ray Diffraction.

Example 4

Batch Testing of 1 h, 2 h and 6 h Calcined Limestone 1 g of calcined limestone chips (Example 1, 2 and 3) were mixed with 5 g of Methanol and 5 g of canola oil. The mixture was made in a tube that was closed. The tube was then inserted in a heating bath shaker. The sealed tubes were reacted at 85° C. for 2 hours. After 2 hours the tubes were taken out of the bath cooled down with water. The content of the tubes was then filtered with a 45 um screen The GC sample preparation and conversion obtained and reported in the table 2.0

TABLE 2.0

| | Weight Loss after calcinations (%) | $CaCO_3$ %-w in catalyst | Time of Calcination (h) | %-Conversion to Biodiesel |
|---|---|---|---|---|
| Limestone (Not calcined) | 0 | 97.2 | 0 | 0.1 |
| Example 1 | 40 | 29.5 | 6 | 97.9 |
| Example 2 | 24 | 29.5 | 2 | 97.8 |
| Example 3 | 10 | 71.8 | 1 | 98.0 |

Example 5

Continuous Testing 65 ml of calcined limestone catalyst (Example 1, 2 and 3) were charged in a column. A solution of 50/50 g/g Methanol-Canola Oil was fed through the column at a flow rate of 1 ml/min at 85° C. A total of 42 Bed Volumes of Oil (BV) were passed through the catalyst bed. LHSV oil=0.54 $H^{-1}$ The results of the three columns are in the following tables.

TABLE 3.0

| BV-OIL PASSED | %-CONVERSION TO BIODIESEL | | |
|---|---|---|---|
| | Example 1 | Example 2 | Example 3 |
| 5 | 96.7 | 97.5 | 97.7 |
| 9 | 98.3 | 98.3 | 97.9 |
| 14 | 98.4 | 98.2 | 98.5 |
| 18 | 98.3 | 97.9 | 98.2 |
| 25 | 97.1 | 97.5 | 97.7 |
| 42 | 97.3 | 98.3 | 97.9 |

TABLE 4.0

| BV-OIL PASSED | %-VOLUME EXPANSION | | |
|---|---|---|---|
| | Example 1 | Example 2 | Example 3 |
| 5 | 0 | 0 | 0 |
| 9 | 3 | 15 | 0 |
| 18 | 65 | 37 | 2 |

TABLE 4.0-continued

| BV-OIL PASSED | %-VOLUME EXPANSION | | |
|---|---|---|---|
| | Example 1 | Example 2 | Example 3 |
| 25 | 87 | 41 | 4 |
| 42 | 100 | 46 | 4 |

TABLE 5.0

| BV-OIL PASSED | PRESSURE (psi) | | |
|---|---|---|---|
| | Example 1 | Example 2 | Example 3 |
| 5 | 28 | 35 | 28 |
| 9 | 28 | 35 | 30 |
| 14 | 23 | 38 | 30 |
| 18 | 27 | 27 | 34 |
| 25 | 37 | 35 | 28 |
| 42 | 53 | 37 | 32 |

Note:
Example 1 had an excessive pressure (53 psi) at the end of the run. This corresponded to blockage of the flow due to the excessive expansion of the catalyst inside the column.

Example 6

Purification of Biodiesel 4 liters of column effluent from Example 5 were filtered through a 45 um screen, and two layers were obtained. The methanol was distilled and two layers were observed. The bottom layer was the glycerol and the top layer was the biodiesel. The bottom layer was separated. The top layer was further purified through a column of Amberlite™ BD 10 resin. The resulting biodiesel is of high quality and complies with the actual ASTM D6584 parameters such as Total Glycerine (specification<0.24%), Free Glycerine (specification<0.02%), Acid Number (<0.02 mg KOH/g), Na and K (<5 ppm), Ca and Mg (<5 ppm).

| Total Glycerine: | 0.0% (w/w) |
| Free Glycerides: | 0.16% (w/w) |
| Acid Number: | 0.02 mg KOH/g |
| Na + K (ppm): | 1 ppm |
| Mg + Ca (ppm): | 3 ppm |

Example 7

Continuous Testing-Columns-Low Methanol Charge 40 ml of calcined limestone catalyst (Example 1, 2 and 3) were charged in a column. A solution of 30/70 (g/g) Methanol-Canola Oil was fed through the column at a flow rate of 1 ml/min at 65° C. A total of 42 Bed Volumes of Oil (BV) were passed through the catalyst bed. LHSV oil=1.05 $h^{-1}$ All the effluent was collected in a container. The total conversion was 97.8% by GC

TABLE 6.0

| BV-OIL PASSED | %-CONVERSION TO BIODIESEL |
|---|---|
| 5 | 97.5 |
| 14 | 98.4 |
| 25 | 97.8 |
| 42 | 97.2 |

Biodiesel Quality:

| Total Glycerine: | 0.0% (w/w) |
| Free Glycerides: | 0.14% (w/w) |
| Acid Number: | 0.03 mg KOH/g |
| Na + K (ppm): | 2 ppm |
| Mg + Ca (ppm): | 2 ppm |

We claim:

1. A solid heterogeneous transesterification catalyst composition comprising:
   a calcined calcium carbonate mixture wherein the calcined calcium carbonate mixture comprises
   i) calcium carbonate wherein the calcium carbonate has a mean crystal size in the range of 450-490 Å and is present in the mixture in an amount in the range of 70-95% based on total weight of the mixture;
   ii) calcium oxide wherein the calcium oxide has a mean crystal size in the range of 190-200 Å and is present in the mixture in an amount in the range of 5-25% based on total weight of the mixture; and
   iii) calcium hydroxide wherein the calcium hydroxide has a mean crystal size in the range of 160-250 Å and is present in the mixture in an amount of less than 5% by weight based on total weight of the mixture.

2. The solid heterogeneous transesterification catalyst composition of claim 1 wherein the calcium carbonate content in the mixture is at least 75% by weight.

3. A solid heterogeneous transesterification catalyst composition comprising:
   a calcined calcium carbonate mixture wherein the calcined calcium carbonate mixture comprises
   i) calcium carbonate wherein the calcium carbonate has a mean crystal size in the range of 450-490 Å and is present in the mixture in an amount in the range of 0-72% based on total weight of the mixture;
   ii) calcium oxide wherein the calcium oxide has a mean crystal size in the range of 190-200 Å and is present in the mixture in an amount in the range of 23-74% based on total weight of the mixture; and
   iii) calcium hydroxide wherein the calcium hydroxide has a mean crystal size in the range of 160-250 Å and is present in the mixture in an amount 4-25% based on total weight of the mixture.

4. The solid heterogeneous transesterification catalyst composition of claim 3, wherein
   i) the calcium carbonate is present in the mixture in an amount in the range of 46-72% based on total weight of the mixture;
   ii) the calcium oxide is present in the mixture in an amount in the range of 23-35% based on total weight of the mixture; and
   iii) the calcium hydroxide is present in the mixture in an amount 4-19% based on total weight of the mixture.

* * * * *